United States Patent
Rhee et al.

(10) Patent No.: US 6,858,251 B2
(45) Date of Patent: *Feb. 22, 2005

(54) LANTHANUM COMPLEX AND PROCESS FOR THE PREPARATION OF A BLT LAYER USING SAME

(75) Inventors: Shi-Woo Rhee, Pohang-si (KR); Sang-Woo Kang, Seoul (KR)

(73) Assignee: Postech Foundation (KR)

( * ) Notice: Subject to any disclaimer, the term of this patent is extended or adjusted under 35 U.S.C. 154(b) by 225 days.

This patent is subject to a terminal disclaimer.

(21) Appl. No.: 10/143,355

(22) Filed: May 9, 2002

(65) Prior Publication Data

US 2003/0059536 A1 Mar. 27, 2003

(30) Foreign Application Priority Data

Sep. 4, 2001 (KR) ......................................... 2001-54054

(51) Int. Cl.[7] .......................... C23C 16/06; C23C 16/14; C23C 16/22
(52) U.S. Cl. ........................... 427/255.36; 427/255.391; 427/255.394
(58) Field of Search .............................. 427/248.1, 250, 427/255.29, 255.36, 255.391, 255.394

(56) References Cited

U.S. PATENT DOCUMENTS 6,274,195 B1 * 8/2001 Rhee et al. ............ 427/255.31

* cited by examiner

*Primary Examiner*—Shrive P. Beck
*Assistant Examiner*—William Phillip Fletcher, III
(74) *Attorney, Agent, or Firm*—Anderson Kill & Olick, P.C.

(57) ABSTRACT

A lanthanum complex of formula (I) having a low evaporation temperature can be used as a useful precursor for MOCVD of a BLT thin layer on semiconductor devices.

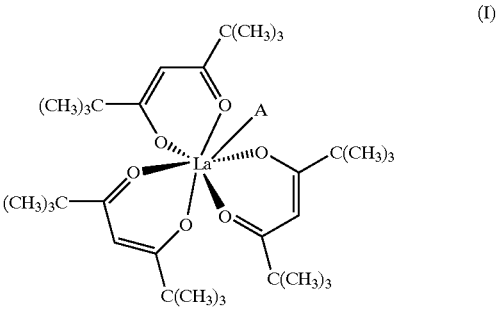

wherein A is pentamethyldiethylenetriamine(PMDT) or triethoxytriethyleneamine(TETEA).

6 Claims, 7 Drawing Sheets

LANTHANUM COMPLEX AND PROCESS FOR THE PREPARATION OF A BLT LAYER USING SAME

FIELD OF THE INVENTION

The present invention relates to a lanthanum complex which exhibits improved solubility in an organic solvent, high vapor pressure and excellent deposition property; and a metal organic chemical vapor deposition (MOCVD) method for preparing a bismuth lanthanum titanate (BLT, $Bi_{4-x}La_xTi_3O_{12}(0<x<4)$) thin layer under a mild condition using said La complex together with appropriate Bi and Ti precursors.

BACKGROUND OF THE INVENTION

Semiconductor devices have recently become more highly integrated and smaller in size than ever before, which generated needs to develop sophisticated materials and processes for forming thin films in the fabrication of semiconductor devices.

A ferroelectric BLT layer is known to have better performance characteristics as compared with other ferroelectric layers. For example, a strontium bismuth titanate (SBT, $SrBi_2Ti_2O_9$) layer requires a high crystallization temperature of 800° C. or higher, and a lead zirconate titanate (PZT, $PbZr_xTi_{1-x}O_3(0<x<1)$) layer exhibits early fatigue only at $10^6$ cycles. In contrast, it is reported that a BLT layer needs a relatively low crystallization temperature of around 700° C., and that it exhibits no sign of fatigue even at $10^{10}$ cycles (see [B. H. Park, B. S. Kang, S. D. Bu, T. W. Noh, J. Lee, and W. Jo, Nature, 401(14), 682(1999)]).

Of various methods of preparing such ferroelectric thin films, MOCVD is the most preferred for the reasons that: it can be carried out at a relatively low temperature; the composition and deposition rate of the thin film can be readily controlled by changing the amounts of the source materials and the carrier gas; and the deposited thin film has good uniformity, excellent conformal step coverage and improved hole filling property without damaging the surface of the substrate.

Generally, a precursor for MOCVD is required to have such properties as high thermostability, non-toxicity, a high vapor pressure and a high deposition rate. Especially preferred is a MOCVD mode carried out by direct liquid injection (DLI) of a soluble precursor dissolved in a solvent. In case of forming a ferroelectric thin layer by DLI, it is preferred that the corresponding metal precursors do not undergo chemical reactions in solution.

However, among conventional organometallic compounds applied to MOCVD for a BLT thin layer, a representative Ti precursor, $Ti(i-OPr)_4$ (titanium tetraisopropoxide), is very sensitive to moisture, and a representative La precursor, $La(tmhd)_3$ (lanthanum tetramethylheptanedionate), exhibits a very low solubility in an organic solvent.

SUMMARY OF THE INVENTION

Accordingly, it is an object of the present invention to provide an La complex which exhibits a high vapor pressure, excellent deposition property and a high solubility in an organic solvent.

It is another object of the present invention to provide an MOCVD process for preparing a BLT thin layer under a mild condition using said La complex.

In accordance with one aspect of the present invention, there is provided a lanthanum complex of formula (I):

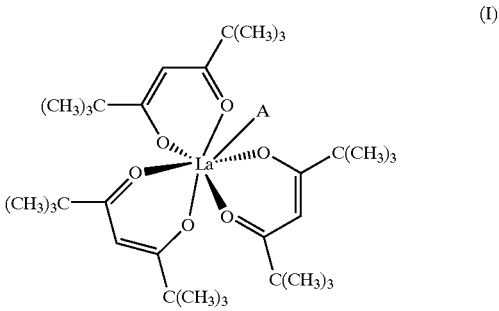

wherein A is pentamethyldiethylenetriamine(PMDT) or triethoxytriethyleneamine(TETEA).

In accordance with another aspect of the present invention, there is provided a process for depositing a BLT($Bi_{4-x}La_xTi_3O_{12}(0<x<4)$) thin layer on a substrate which comprises bringing the vapors of said La complex, a Ti precursor of formula (II) and an organobismuth(Bi) precursor into contact with the substrate:

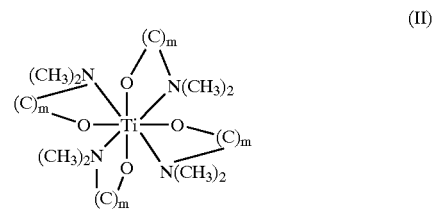

wherein m is an integer ranging from 2 to 5.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1A:
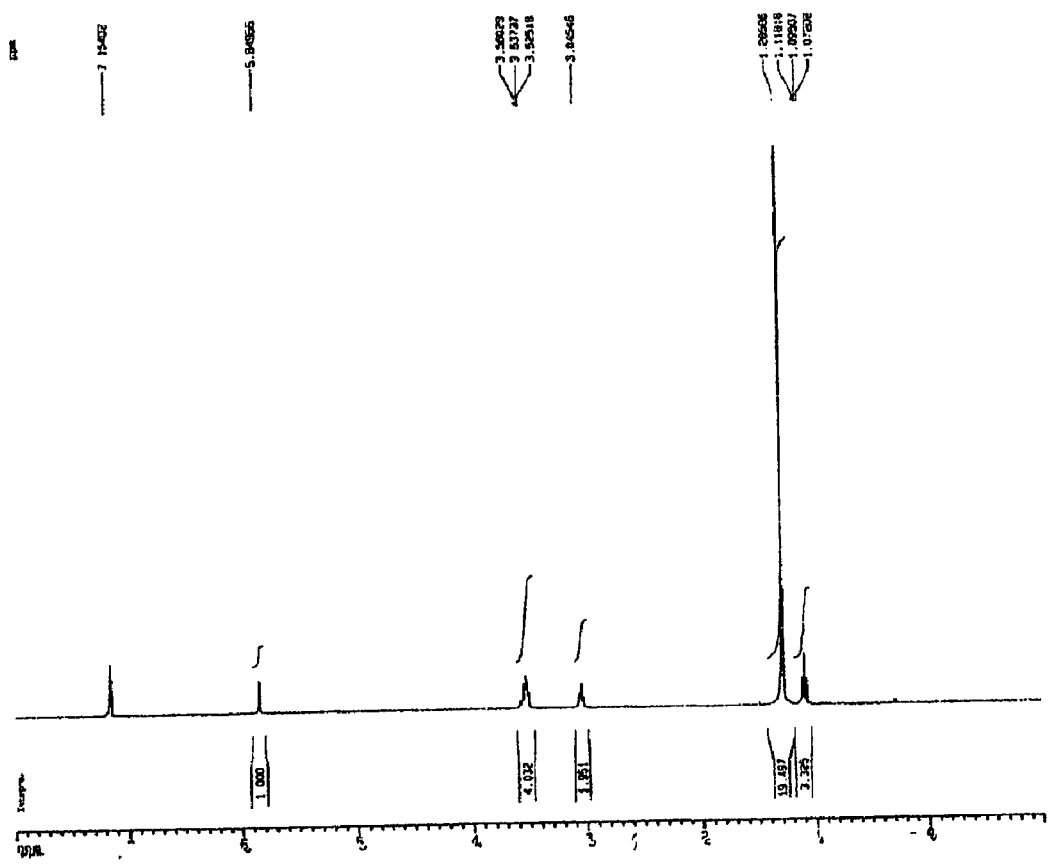
FIGS. 1A and 1B: $^1$H-NMR and TGA/DSC scans of La(tmhd)$_3$-TETEA obtained in Example 1 of the present invention.

The La complex of formula (I) of the present invention can be prepared by reacting La(tmhd)$_3$ with pentamethyldiethylenetriamine(PMDT) or triethoxytriethyleneamine (TETEA) in an organic solvent such as hexane at room temperature. The La complex thus prepared has improved deposition property, is highly volatile at a low temperature and dissolves readily in an organic solvent, and thus, it can be used as an excellent La precursor in MOCVD for fabricating a lanthanum-containing thin film.

In practicing the present invention, the MOCVD process for the formation of a BLT thin layer using the inventive La precursor, the Ti precursor of formula (II) and an organobismuth precursor may be carried out by bringing the vapors of the precursors into contact with the surface of a substrate heated to a temperature ranging from 250 to 750° C., preferably 250 to 450° C.

The Ti precursor of formula (II) used in the present invention is preferably Ti(dmae)$_4$(titanium tetradimethylaminoethoxide) of formula (III). Ti(dmae)$_4$ is a liquid at room temperature, easy to handle (see [J. H. Lee et al., *J. Vac. Sci. Technol.*, 17(1999), 3033]), and less sensitive to air or moisture than Ti(i-OPr)$_4$.

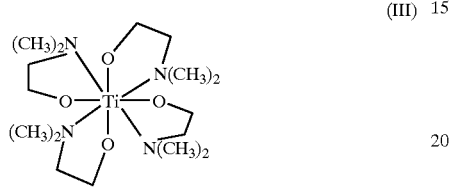

(III)

A preferred example of the organobismuth precursor which may be used in the present invention is Bi(phenyl)$_3$.

In the inventive MOCVD process, such La, Ti and Bi precursors may be vaporized by direct liquid injection (DLI) or bubbling.

In case of DLI, each precursor may be dissolved in an organic solvent and the solution is injected into an evaporator maintained at a temperature ranging from 100 to 300° C., vaporizing the precursor under an appropriate carrier gas flow. In preparing the injection solution, an organic solvent such as n-butylacetate, heptane, octane, tetrahydrofuran (THF) and the like may be used. Since the La, Ti and Bi precursors of the present invention do not chemically interact with each other in a single solution phase, an injection solution containing two or all three precursors may also be used.

The bubbling delivery may be carried out by passing a carrier gas through a precursor held in a container(bubbler) maintained at an appropriate temperature, e.g., room temperature to 200° C., to transport the resulting precursor-containing vapor into a reactor. The carrier gas used in this process may be an inert gas such as argon and nitrogen. If necessary, the precursor vapor alone may be transported without the use of a carrier gas.

In accordance with the present invention, a BLT thin layer deposited by the inventive method may be heat treated to impart crystallinity thereinto. The substrate which can be used in the present invention includes silicon, Pt, Ir, IrO$_2$, Ru, RuO$_2$ and others. The thickness of the BLT layer may be conveniently controlled by adjusting the deposition time.

The following Examples are given for the purpose of illustration only, and are not intended to limit the scope of the invention.

EXAMPLE 1

Preparation of La(tmhd)$_3$-TETEA and La(tmhd)$_3$-PMDT

La(tmhd)$_3$(0.0143 mole) and triethoxytriethyleneamine (TETEA, 0.0143 mole) were dissolved in hexane, and the solution was kept at room temperature for 12 hrs. Then, the reaction mixture was filtered and the solvent was removed from the filtrate under a reduced pressure, to give La(tmhd)$_3$-TETEA as a solid.

The above procedure was repeated using pentamethyldiethylenetriamine(PMDT) instead of TETEA, to give La(tmhd)$_3$-PMDT as a solid.

Figure 1B:
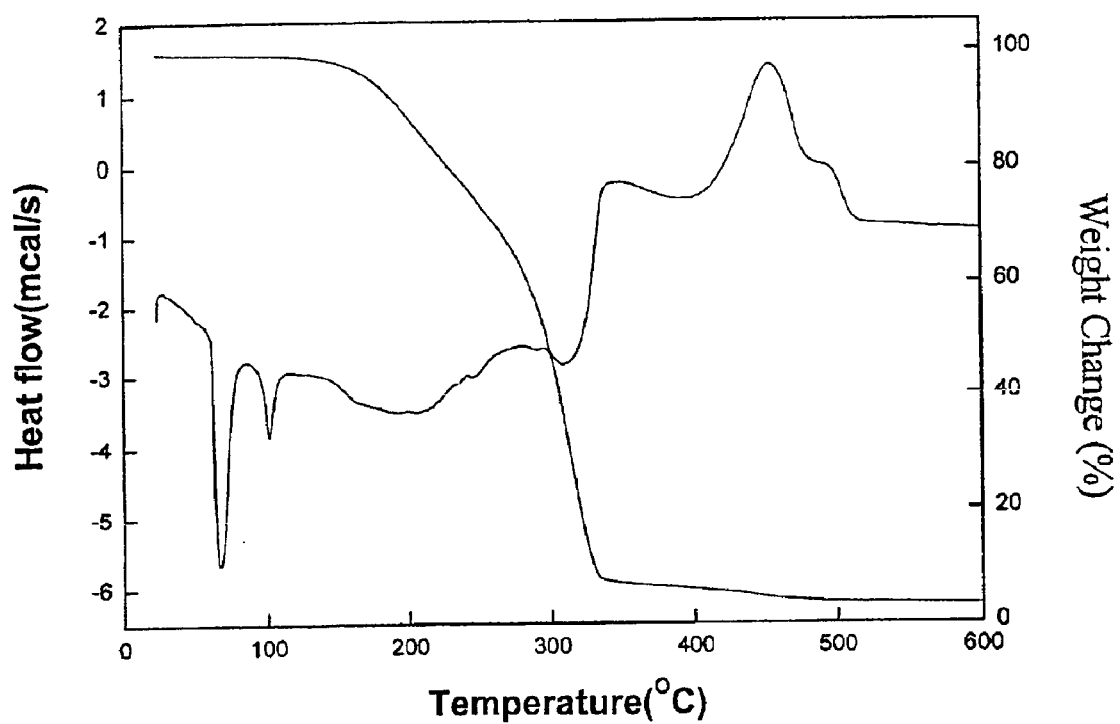
Figure 2A:
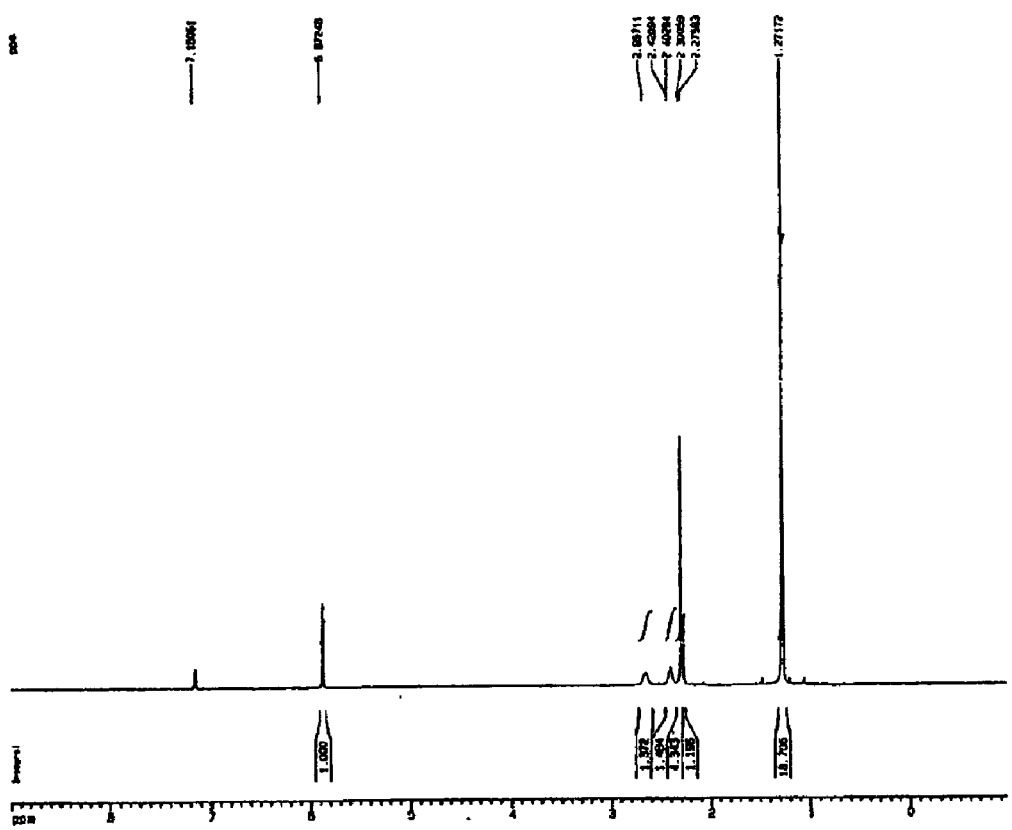
FIGS. 2A and 2B: $^1$H-NMR and TGA/DSC scans of La(tmhd)$_3$-PMDT obtained in Example 1 of the present invention.
Figure 2B:
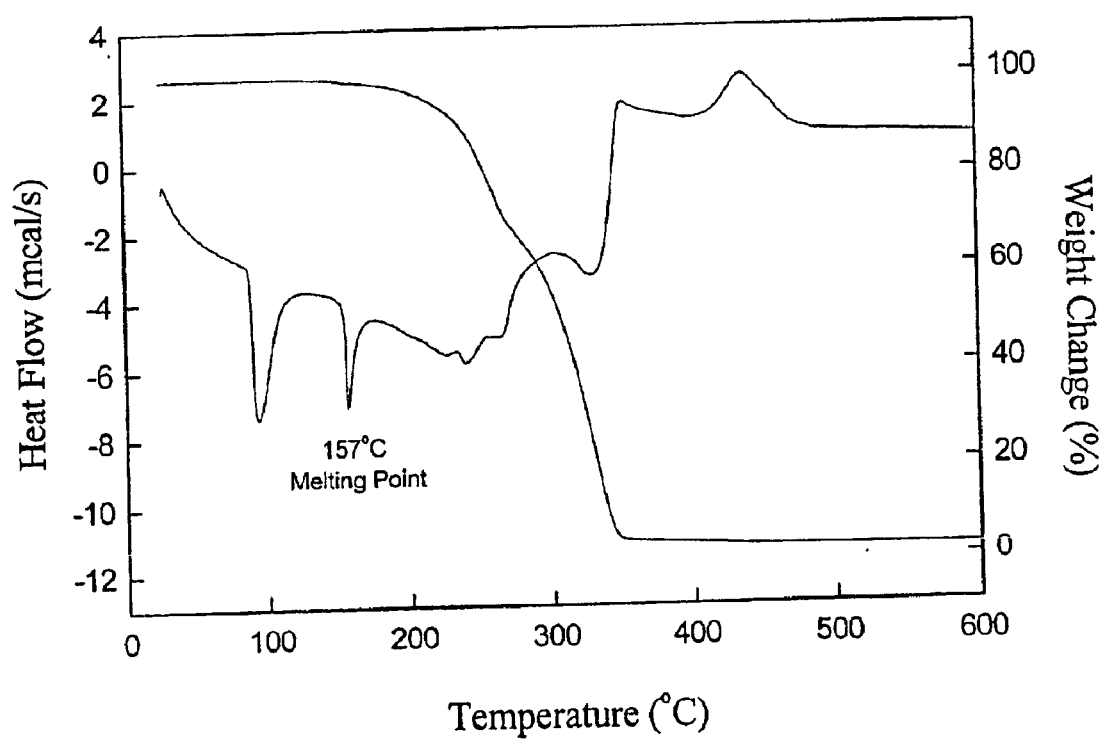
Figure 3:
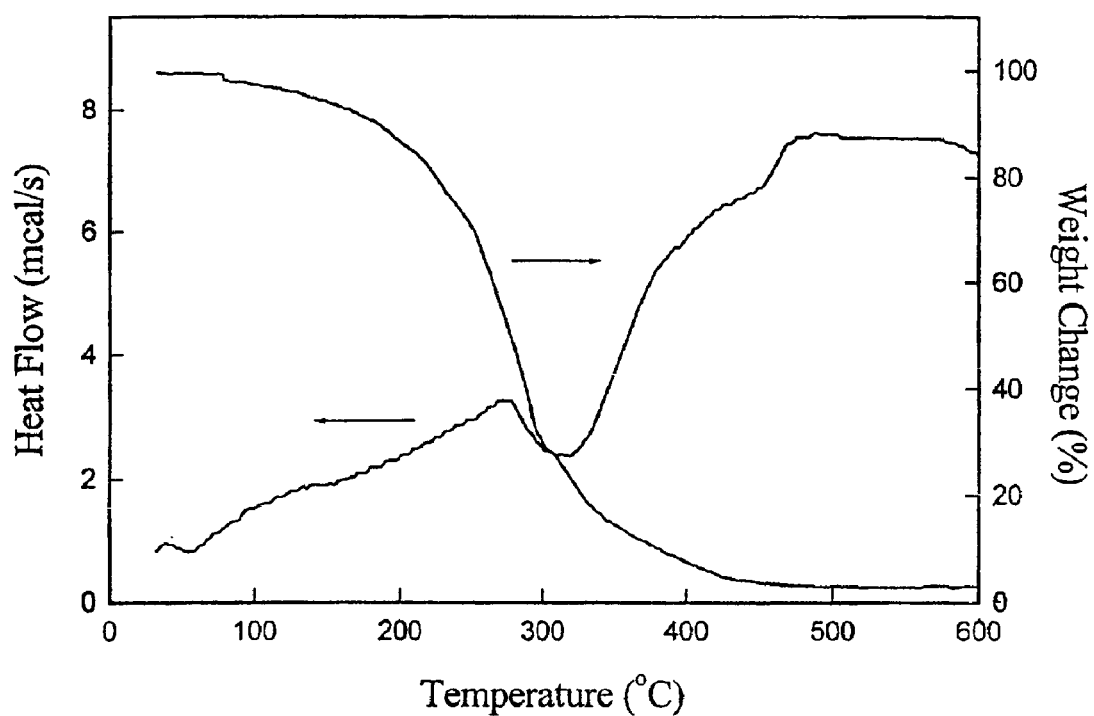
FIG. 3: TGA/DSC scans of Ti(dmae)$_4$.
Figure 4:
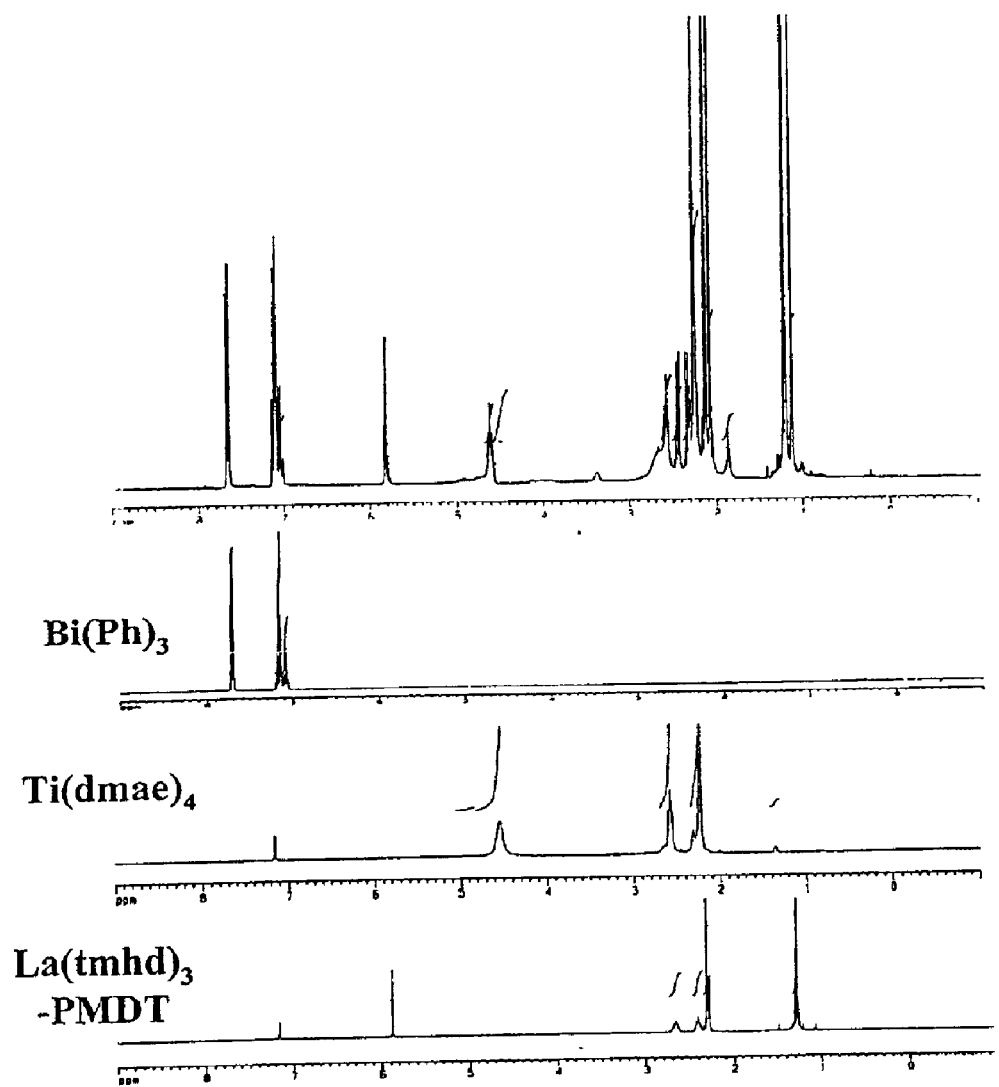
FIG. 4: $^1$H-NMR spectrum of a solution containing Ti(dmae)$_4$, La(tmhd)$_3$-PMDT and Bi(phenyl)$_3$, as described in Example 2 of the present invention.

$^1$H-NMR and TGA/DSC scans of La(tmhd)$_3$-TETEA thus obtained are shown in FIGS. 1A and 1B, respectively; and those of La(tmhd)$_3$-PMDT, in FIGS. 2A and 2B, respectively. For reference, TGA/DSC scans of Ti(dmae)$_4$ used as a Ti precursor in the present invention are shown in FIG. 3. The results suggest that the La and Ti complexes used in the present invention are thermally stable.

EXAMPLE 2

Deposition of BLT Thin Layer

A BLT thin film was formed on a Pt/TiO$_2$/SiO$_2$/Si substrate by MOCVD employing La(tmhd)$_3$-PMDT obtained in Example 1, Ti(dmae)$_4$ and Bi(phenyl)$_3$ as follows.

0.2M solutions of La(tmhd)$_3$-PMDT, Ti(dmae)$_4$ and Bi(phenyl)$_3$ in N-butylacetate were mixed in a volume ratio of 1:1:4 and injected into the vaporizer of an MOCVD apparatus at a rate of 0.1 ml/min. The deposition was conducted under the conditions of evaporation temperature (vaporizer) of 240° C., carrier gas flow rate of Ar/O$_2$ 200/400(sccm), reactor pressure of 2 torr, vaporizer pressure of 5 torr and substrate temperature of 400° C., to prepare a 1,000 Å-thick BLT thin layer.

The injection solution containing the precursors was stored for 3 days and examined by $^1$H-NMR. The result demonstrates that these precursors in solution had not undergone any reaction during the 3 day storage.

Figure 5A:
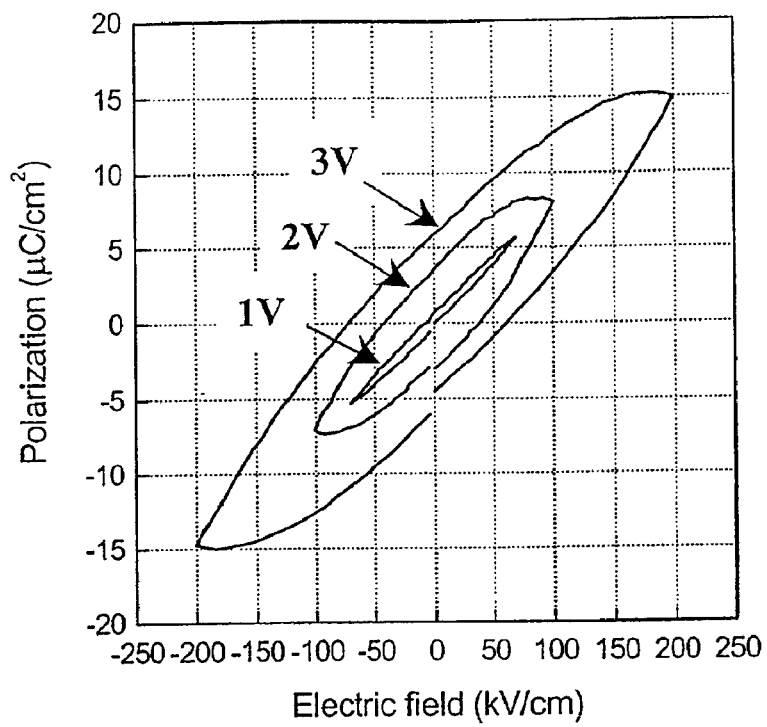
FIGS. 5A and 5B: electrical properties of the deposited and heat-treated BLT layers, respectively, as described in Example 2 of the present invention.
Figure 5B:
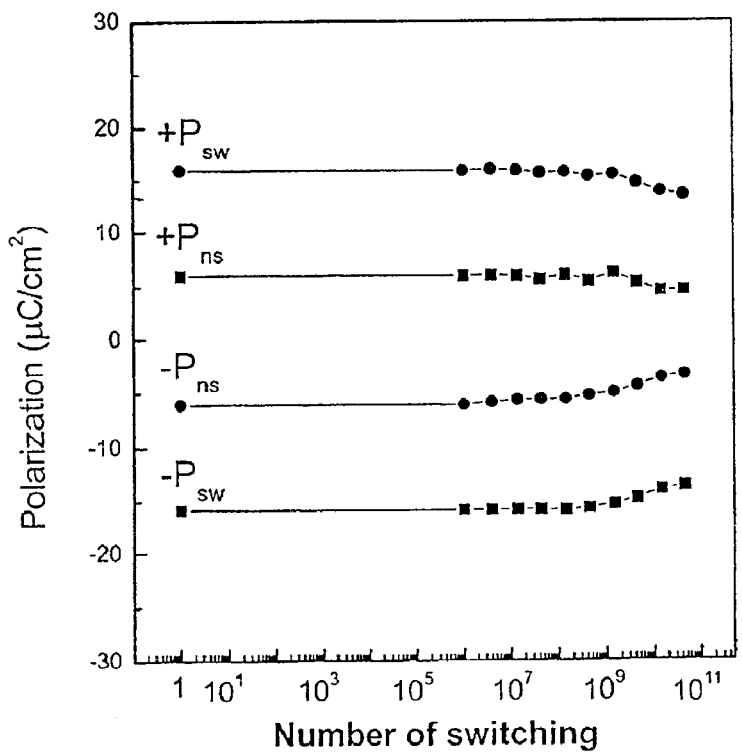

After the BLT thin layer deposited was heat-treated at 650° C. for 1 hr, its electrical properties were measured. The results are shown in FIGS. 5A and 5B, which exhibits improved polarization values and fatigue property(sw=switched state, ns=non-switched state), suitable for use in manufacturing a semiconductor device such as a ferroelectric random access memory(FRAM).

Therefore, the La complex of the present invention, which has all the desirable improved properties in terms of thermal stability, volatility, solubility in organic solvents and others, can be advantageously used as a useful La precursor for MOCVD in the deposition of a BLT thin layer under a mild condition.

While the invention has been described with respect to the above specific embodiments, it should be recognized that various modifications and changes may be made to the invention by those skilled in the art which also fall within the scope of the invention as defined by the appended claims.

What is claimed is:

1. A process for depositing a BLT(Bi$_{4-x}$La$_x$Ti$_3$O$_{12}$ (0<x<4)) thin layer on a substrate which comprises bringing the vapors of an La complex of formula (I), a Ti precursor of formula (II) and an organobismuth(Bi) precursor into contact with the substrate:

(I)

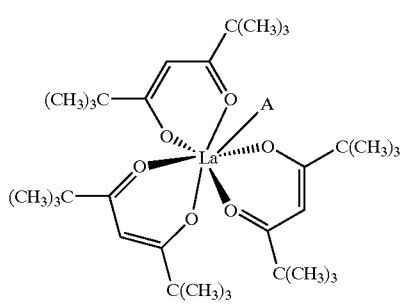

(II)

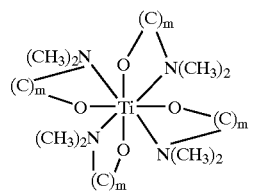

wherein A is pentamethyldiethylenetriamine(PMDT) or triethoxytriethyleneamine(TETEA), and m is an integer ranging from 2 to 5.

2. The process of claim 1, wherein the substrate was heated to a temperature ranging from 250 to 750° C.

3. The process of claim 1, wherein the precursor vapors are generated by dissolving the precursors in an organic solvent and subjecting the solution to a temperature ranging from 100 to 300° C.

4. The process of claim 1, wherein the precursor vapors are generated by evaporating the precursors at a temperature of room temperature to 200° C.

5. The process of claim 1, wherein the Ti precursor is $Ti(dmae)_4$(titanium tetradimethylaminoethoxide).

6. The process of claim 1, wherein the Bi precursor is $Bi(phenyl)_3$.

* * * * *